US00PP14834P2

(12) United States Plant Patent
Jackson

(10) Patent No.: US PP14,834 P2
(45) Date of Patent: May 25, 2004

(54) ERIGERON PLANT NAMED 'SPINDRIFT'

(50) Latin Name: *Erigeron karvinskianus*
Varietal Denomination: Spindrift

(76) Inventor: Bryan Jackson, 810-834 Springvale Rd., Braeside, Victoria 3195 (AU)

( * ) Notice: Subject to any disclaimer, the term of this patent is extended or adjusted under 35 U.S.C. 154(b) by 0 days.

(21) Appl. No.: 10/366,017

(22) Filed: Feb. 13, 2003

(51) Int. Cl.[7] ..... A01H 5/00
(52) U.S. Cl. ..... Plt./263
(58) Field of Search ..... Plt./263

*Primary Examiner*—Anne Marie Grunberg

(57) ABSTRACT

A new cultivar of Erigeron named 'Spindrift' that is distinguishable by medium green foliage, a compact mounding habit and small daisy-like flowers that range in color from dark purple to lilac-pink and white. In combination these traits set 'Spindrift' apart from all other existing varieties of Erigeron known to the inventor.

2 Drawing Sheets

Genus: Erigeron.
Species: *karvinskianus.*
Denomination: 'Spindrift'.

BACKGROUND OF THE INVENTION

The present invention relates to a new and distinct cultivar of Santa Barbara daisy and is an herbaceous perennial that is grown for use as an ornamental landscape and container plant. The new invention is known botanically as *Erigeron karvinskianus* and will be referred to hereinafter by the cultivar name 'Spindrift'. Erigeron is in the family Compositae in which the commonly referred to "flower", is actually the inflorescence, and made up of smaller ray flowers and disc florets. For ease of clarification the common term "flower" is used herein to describe the inflorescene.

'Spindrift' is an induced mutation that was bred by the inventor in January 1998 in a cultivated area of Victoria, Australia. In March 1997 the inventor treated ten *Erigeron karvinskianus* plants with Colchicine. Colchicine was used to change the chromosome count of the plant. Dwarfing can be a side effect of the chemical and was critical to the breeding process. In January 1998 the seed from these plants was collected and sown. The inventor selected 'Spindrift' in 1998, from the seedlings that resulted, based on its compact growth habit. The female parent plant is *Erigeron karvinskianus* (unpatented) and the male parent plant is *Erigeron karvinskianus.* 'Spindrift' differs from the parent plant in growth habit and fertility.

'Spindrift' is a ground cover and container plant that exhibits a compact mounding habit with small daisy-like flowers that bloom year round. Flowers exhibiting the colors of white, pink-lilac and dark purple-rose are all individually present on an individual plant. 'Spindrift' is hardy to minus 2° Centigrade and cultural requirements include full sun to light shade and moist well-draining soil. The distinguishing characteristics of 'Spindrift' are habit and low fertility. The closest comparison plant is the parent plant *Erigeron karvinsiana.* 'Spindrift' is distinguishable from the parent plant by growth habit and low fertility.

The first asexual reproduction of 'Spindrift' was carried out by the inventor in 1998 in a cultivated area of Melbourne, Australia. The method used was softwood cuttings. Since that time subsequent generations have been determined stable and true to type.

SUMMARY OF THE INVENTION

The following traits have been repeatedly observed and represent the distinguishing characteristics of the new Erigeron cultivar. These traits in combination distinguish 'Spindrift' from all other existing varieties of Erigeron known to the inventor. 'Spindrift' has not been tested under all possible conditions and phenotypic differences may be observed with variations in environmental, climatic, and cultural conditions, however, without any variance in genotype.

1. Erigeron 'Spindrift' is an herbaceous perennial exhibiting a compact, mounding growth habit.
2. Erigeron 'Spindrift' produces small daisy-like flowers that exhibit the colors dark purple-rose, lilac-pink, and white all individually present on an individual plant.
3. Erigeron 'Spindrift' exhibits low fertility.
4. Erigeron 'Spindrift' exhibits medium-green foliage.
5. Erigeron 'Spindrift' is 16 cm. in height and 40 cm. in width in a 2-litre container.
6. Erigeron 'Spindrift' is floriferous and moderately vigorous.
7. Erigeron 'Spindrift' continues blooming year round.
8. Erigeron 'Spindrift' is hardy to minus 2° Centigrade.

BRIEF DESCRIPTION OF THE DRAWINGS

The accompanying color drawings illustrate the overall appearance of the new Erigeron variety 'Spindrift' showing the colors as true as it is reasonably possible to obtain in colored reproductions of this type. The drawings were made in September 2002 of plants grown out-of-doors in a cultivated area of Breaside, Victoria, Australia. The plants were 2 years old at the time and grown out-of-doors in the ground.

The drawing on sheet 1 illustrates the entire plant in bloom from a front perspective.

The drawing on sheet 2 illustrates a close-up view of the flowers. Colors in the photographs may differ from the color values cited in the detailed botanical description, which more accurately describes the actual colors of the new variety 'Spindrift'. Drawings were made using conventional techniques and although flower and foliage colors may appear different from actual colors due to light reflectance, they are as accurate as possible by conventional photography.

BOTANICAL DESCRIPTION OF THE PLANT

The following is a detailed botanical description of the new Erigeron variety 'Spindrift'. Observations, measurements, values and comparisons were taken in Arroyo Grande Calif. from 6-month-old plants grown out-of-doors in 2-litre containers. Color determinations are made in accordance with The 2001 Royal Horticultural Society Colour Chart from London England, except where general color terms of ordinary dictionary significance are used. The Compositae family, under which Erigeron falls, exhibits an inflorescence which is commonly referred to as the "flower". In actuality smaller ray flowers and disc florets make up the inflorescence. For ease of clarification the common term "flower" is used here to designate a category of description. Under this category is the detailed botanical description of the parts of the inflorescence, which is commonly referred to as the flower on this plant.

Botanical classification: Erigeron 'Spindrift'.
Species: *karvinskianus.*
Common name: Santa Barbara daisy.
Parentage: Erigeron 'Spindrift' is an induced mutation that resulted from the induced hybridization of the following parent plants:
*Seed parent plant.*—*Erigeron karvinskianus.*
*Pollen parent.*—*Erigeron karvinsianus.*
Propagation method: Softwood cuttings.
Rooting habit: Fine.
Time to develop roots: Approximately 10 days are needed for an initial cutting to develop roots.
Ideal temperatures to initiate rooting: Recommended air temperature is between 15° Centigrade and 25° Centigrade.
Crop time: 4–6 months are needed to produce a finished 2-litre container from a rooted cutting.
Growth habit: Compact and mounding.
Suggested container size: 2-litre container.
Use: Ornamental landscape plant for use as a ground cover, in perennial borders or as a container plant.
Type: Herbaceous perennial.
Vigor: Moderately vigorous.
Height of plant: 16 cm. in height in a 2-litre container.
Width of plant: 40 cm. in width in a 2-litre container.
Cultural requirements: Grow in full sun or light shade with moderate water and good drainage.
Hardiness: Hardy to minus 2° Centigrade.
Other: Exhibits low fertility.
Diseases and pests: Potential for mild infestation of aphids.
Stem:
*Branching habit.*—Basal branching.
*Stem color.*—138B.
*Stem dimensions.*—10 cm in length and 1 mm. in width.
*Stem shape.*—Cylindrical.
*Stem surface.*—Puberulent.
*Internode length.*—Internode length is 5 cm.
Foliage:
*Type.*—Evergreen.
*Leaf arrangement.*—Alternate.
*Single or compound.*—Single.
*Leaf division.*—Simple.
*Margin.*—Entire.
*Leaf shape.*—Oblanceolate.
*Leaf length.*—1.50 cm. in length.
*Leaf width.*—0.50 cm. in width.
*Leaf base.*—Attenuate.
*Leaf apex.*—Aristulate.
*Leaf venation pattern.*—Parallel.
*Vein color* (*abaxial surface*).—138C.
*Vein color* (*adaxial surface*).—138C.
*Leaf surface* (*abaxial surface*).—Glabrous.
*Leaf surface* (*adaxial surface*).—Glabrous.
*Leaf attachment.*—Petiolate.
*Petiole dimensions.*—6 mm. in length and 1 mm. in diameter.
*Petiole shape.*—Sulcate.
*Petiole color.*—138B.
*Petiole surface.*—Pubescent.
*Presence of stipules or spines.*—None.
*Leaf color* (*adaxial surface*).—138A.
*Leaf color* (*abaxial surface*).—138B.
*Fragrance.*—The foliage has no fragrance.
Flower:
*Inflorescence.*—Terminal and solitary inflorescence.
*Aspect.*—Facing upward and outward.
*Dimensions of inflorescence.*—The size of an individual inflorescence present on an individual plant can range from 0.75 cm. in length and 1 cm. in diameter to 0.75 cm. in length and 1.75 cm. in diameter.
*Inflorescence type.*—Capitula radiate.
*Quantity of inflorescences per plant.*—Approximately 150.
*Natural flowering season.*—All seasons. Plants bloom year round.
*Peduncle dimensions.*—10 cm in length and 1 mm. in width.
*Peduncle shape.*—Cylindrical.
*Peduncle surface.*—Puberulent.
*Peduncle color.*—139C.
*Shape of immature inflorescence* (*bud*).—Obconical.
*Dimensions of immature inflorescence* (*bud*).—5 mm. in diameter and 5 mm. in length.
*Color of immature inflorescence* (*bud*).—138B.
*Self-cleaning or persistent.*—Self-cleaning.
*Ray flower texture* (*both adaxial and abaxial surfaces*).—Petaloid and slightly furrowed.
*Ray flower surface* (*abaxial surface*).—Glabrous.
*Ray flower surface* (*adaxial surface*).—Glabrous.
*Pubescence.*—None present.
*Ray flower arrangement.*—Radiate.
*Number of ray flowers.*—Approximately 8 in number.
*Fused or unfused.*—Unfused.
*Ray flower margins.*—Entire.
*Ray flower shape.*—Closest to oblanceolate.
*Ray flower apex.*—Acute.
*Ray flower base.*—Attenuate.
*Ray flower dimensions.*—9 mm. in length and 1.5 mm. in width.
*Ray flower color* (*adaxial surface*).—The color of ray flowers on an individual plant is a combination of the darkest colors, which are 77A and 77B, and the lighter colors 76C and N155B.
*Ray flower color* (*abaxial surface*).—The color of ray flowers on an individual plant is a combination of the darkest colors, which are 77A and 77B, and the lighter colors 76C and N155B.
*Disc florets.*—Approximately 50.
*Disc floret dimensions.*—0.75 mm. in length and 0.50 mm. in width.
*Surface of disc florets.*—Glabrous.
*Disk floret color.*—Both 153B and 152B exist on the same plant but different inflorescenes.

*Dimensions of phyllary.*—6 mm. in diameter and 3 mm. in length.
*Color of phyllary.*—139C.
*Involucral bract arrangement.*—Cupule.
*Number of involucral bracts.*—20 in number.
*Involucral bract shape.*—Elongated oval.
*Involucral bract margin.*—Entire.
*Involucral bract apex.*—Aristate.
*Involucral bract base.*—Truncate.
*Involucral bract dimensions.*—3 mm. in length and 2 mm. in width.
*Involucral bract color* (*adaxial surface*).—139C.
*Involucral bract color* (*abaxial surface*).—139C.
*Involucral bract surface* (*abaxial surface*).—Pubescent.
*Involucral bract surface* (*adaxial surface*).—Pubescent.
*Fragrance of inflorescence.*—No fragrance present.

Reproductive organs:
*Stamens.*—Approximately five to each disc floret with filaments adnate to the corolla of each disc floret.
*Anther dimensions.*—0.25 mm. in width and 0.50 mm. in length.
*Anther color.*—153B.
*Anther shape.*—Connate.
*Quantity of pollen.*—Moderate amount.
*Pollen color.*—153B.
*Style.*—One to each disc floret.
*Style color.*—152B.
*Style dimensions.*—3 mm. in length and 0.25 mm in width.
*Style shape.*—Filament.
*Stigma shape.*—Two-branched.
*Stigma color.*—152B.
*Ovary position.*—Inferior.
*Ovary dimensions.*—Less than 0.25 mm in length and less than 0.25 mm. in width.
*Ovary color.*—N144B.

Seed:
*Seed color.*—N199B.
*Seed shape.*—Closest to oval.
*Seed dimensions.*—1 mm. in length and 0.50 mm. in width.
*Quantity of seed.*—Many seeds per inflorescence.
*Seed surface.*—Dull and glabrous.

I claim:

1. A new and distinct cultivar of Erigeron plant named 'Spindrift' as described and illustrated.

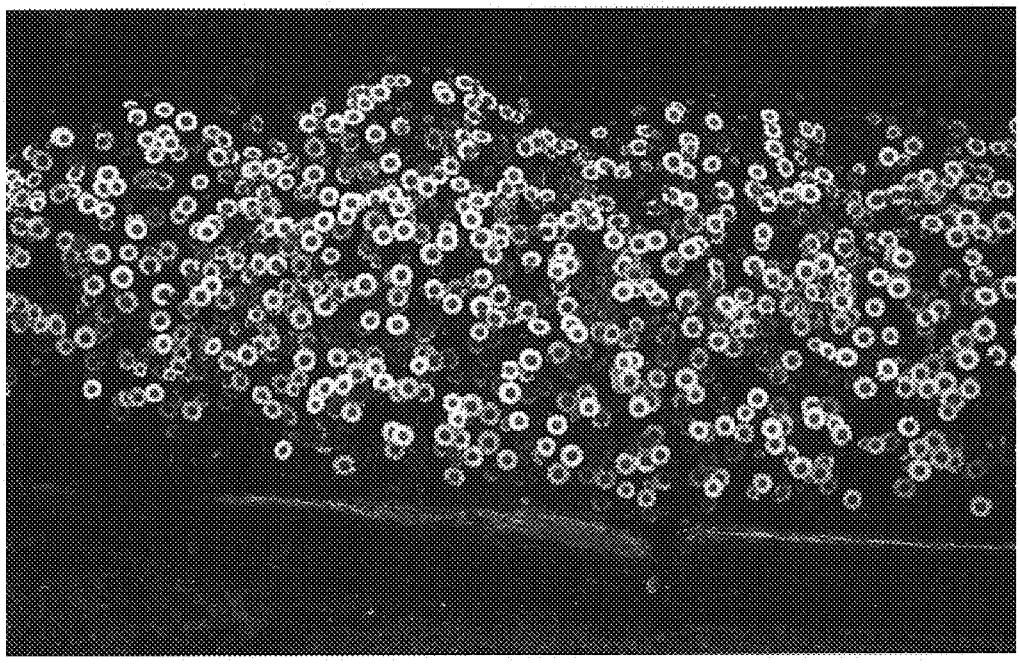

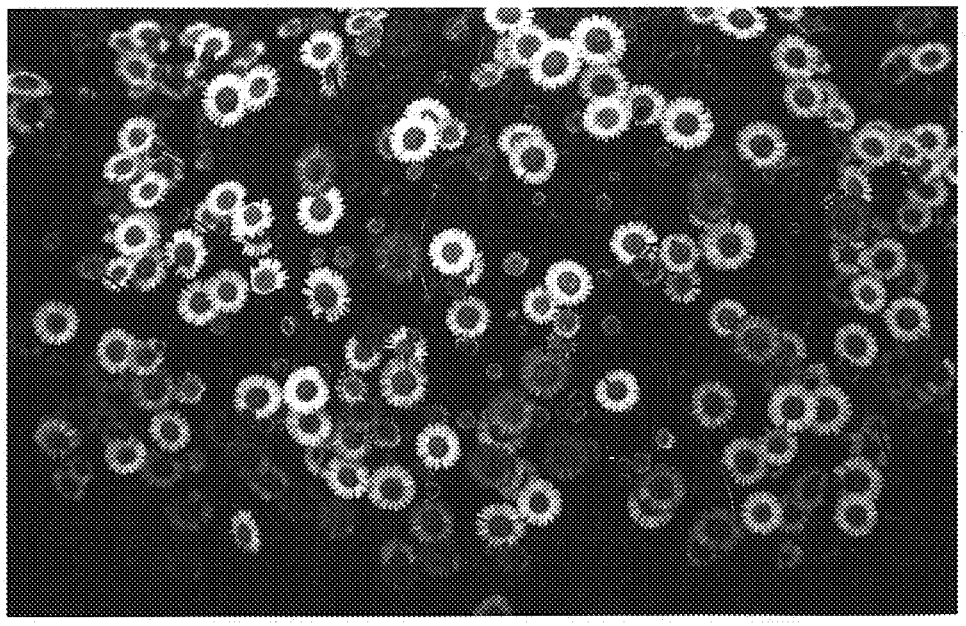

* * * * *